US010512431B2

(12) United States Patent
Cheng et al.

(10) Patent No.: US 10,512,431 B2
(45) Date of Patent: Dec. 24, 2019

(54) SENSOR PATCH AND SENSING DEVICE HAVING THE SAME (71) Applicants: AGENCY FOR SCIENCE, TECHNOLOGY AND RESEARCH, Singapore (SG); SINGAPORE HEALTH SERVICES PTE LTD, Singapore (SG)

(72) Inventors: Ming-yuan Cheng, Singapore (SG); Cairan He, Singapore (SG); Swee Kim Tan, Singapore (SG); Choon Lool Bong, Singapore (SG); Chee Keong Ho, Singapore (SG); Ramona Damalerio, Singapore (SG); Weiguo Chen, Singapore (SG); Yuandong Gu, Singapore (SG)

(73) Assignees: AGENCY FOR SCIENCE, TECHNOLOGY ANO RESEARCH, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 138 days.

(21) Appl. No.: 15/532,994

(22) PCT Filed: Dec. 1, 2015

(86) PCT No.: PCT/SG2015/050480
§ 371 (c)(1),
(2) Date: Jun. 2, 2017

(87) PCT Pub. No.: WO2016/089307
PCT Pub. Date: Jun. 9, 2016

(65) Prior Publication Data
US 2017/0367654 A1 Dec. 28, 2017

(30) Foreign Application Priority Data
Dec. 2, 2014 (SG) .............................. 10201408029P (51) Int. Cl.
*A61B 5/00* (2006.01)
*A61B 5/02* (2006.01)
(Continued)

(52) U.S. Cl.
CPC .............. *A61B 5/6885* (2013.01); *A61B 5/02* (2013.01); *A61B 5/103* (2013.01); *A61B 5/6833* (2013.01);
(Continued)

(58) Field of Classification Search
CPC ......... A61B 5/02; A61B 5/103; A61B 5/6885; A61B 5/6833; A61B 2562/0261
See application file for complete search history.

(56) References Cited

U.S. PATENT DOCUMENTS 3,853,118 A  12/1974  Schendel
5,964,703 A  10/1999  Goodman et al.
(Continued)

FOREIGN PATENT DOCUMENTS

CN  2221418 Y   3/1996
CN  1346974 A   5/2002
(Continued)

OTHER PUBLICATIONS

Gong et al., "A wearable and highly sensitive pressure sensor with ultrathin gold nanowires", Nature Communications, 5:3132 (Year: 2014).*
(Continued)

*Primary Examiner* — Eric F Winakur
*Assistant Examiner* — Chu Chuan Liu
(74) *Attorney, Agent, or Firm* — Womble Bond Dickinson (US) LLP (57) ABSTRACT According to embodiments of the present invention, a sensor patch for detecting extravasation is provided. The sensor patch includes an elastic film, and at least one sensing
(Continued)

electrode disposed on the elastic film, wherein an electrical resistance of the at least one sensing electrode is changeable in response to a force acting on the at least one sensing electrode. According to further embodiments of the present invention, a sensing device is also provided.

17 Claims, 10 Drawing Sheets

(51) Int. Cl.
*A61B 5/103* (2006.01)
*A61M 5/168* (2006.01)

(52) U.S. Cl.
CPC .. *A61B 2562/0261* (2013.01); *A61M 5/16836* (2013.01)

(56) References Cited

U.S. PATENT DOCUMENTS

| | | | |
|---|---|---|---|
| 6,375,624 | B1 | 4/2002 | Uber et al. |
| 6,425,878 | B1 | 7/2002 | Shekalim |
| RE38,695 | E | 2/2005 | Goodman et al. |
| 7,674,244 | B2 | 3/2010 | Kalafut et al. |
| 7,801,583 | B2 | 9/2010 | Brabrand |
| 8,057,406 | B2 | 11/2011 | Mohiuddin |
| 8,904,876 | B2 * | 12/2014 | Taylor ............. G01L 1/18 361/283.4 |
| 2006/0135884 | A1 | 6/2006 | Hack et al. |
| 2011/0137187 | A1 | 6/2011 | Yang et al. |
| 2013/0041235 | A1 * | 2/2013 | Rogers ............. A61B 5/6867 600/306 |
| 2013/0218050 | A1 | 8/2013 | Eichhorn et al. |
| 2015/0059486 | A1 * | 3/2015 | Choong ............. G01L 9/0052 73/727 |

FOREIGN PATENT DOCUMENTS

| | | |
|---|---|---|
| CN | 101226163 A | 7/2008 |
| CN | 201248900 Y | 6/2009 |
| CN | 102506693 A | 6/2012 |
| CN | 103707131 A | 4/2014 |
| CN | 103743438 A | 4/2014 |
| CN | 104880206 A | 9/2015 |
| CN | 107206190 A | 9/2017 |
| WO | WO 1999/0026686 A1 | 6/1999 |
| WO | WO 2002/070044 A1 | 9/2002 |
| WO | WO 2003/063660 A2 | 8/2003 |
| WO | WO 200710124298 A2 | 11/2007 |
| WO | WO 2008/010216 A2 | 1/2008 |
| WO | WO 2009/042624 A2 | 4/2009 |
| WO | WO 2011/041507 A1 | 4/2011 |
| WO | WO 2011/0041607 A1 | 4/2011 |
| WO | WO 2014/128090 A1 | 8/2014 |
| WO | WO 2014/143150 A1 | 9/2014 |

OTHER PUBLICATIONS

Intellectual Property Office of Singapore; Notification of Transmittal of The International Search Report and The Written Opinion of the International Searching Authority, or The Declaration for counterpart International Application No. PCT/SG2015/050480, 10 pgs. (dated Jan. 25, 2016).
Stassi, S., et al., "Flexible Tactile Sensing Based on Piezoresistive Composites: A Review." *Sensors*, Mar. 14, 2014, vol. 14, No. 3, pp, 5296-5332 (DOi:10.3390/s140305296).
Intellectual Property Office of Singapore; International Preliminary Report on Patentability, for counterpart International Application No. PCT/SG2015/050480, 15 pgs. (dated Sep. 29, 2016).
Donghee Son et al., "Multifunctional Wearable devices for diagnosis and therapy of movement disorders," Nature Technology, vol. 9, May 2014, pp. 397-404.
Hee, et al., "Infusion technology: a cause for alarm." Pediatric Anaesthesia, pp. 1-6(12) (2002).
Ming Ying et al., "Silicon Nanomembranes for fingertip electronics," Nanotechnology, 23, 2012, 8 pages.
The Supplementary European Search Report of European Patent Application No. 15 86 4524 completed Jul. 25, 2018, 9 pages.
The First Official Chinese Office Action for Application No. 201580074614.7 dated Oct. 18, 2019, 32 pages.
Wen, C., "Sensor Detection Technology," Higher Vocational Education 12th Five Year Plan Textbook, Feb. 28, 2011, pp. 82-84, Harbin University of Engineering Press.

* cited by examiner

SENSOR PATCH AND SENSING DEVICE HAVING THE SAME

CROSS-REFERENCE TO RELATED APPLICATION

This patent application is a U.S. National Phase application under 35 U.S.C. § 371 of International Application No. PCT/SG2015/050480, filed on Dec. 1, 2015, entitled SENSOR PATCH AND SENSING DEVICE HAVING THE SAME, which claims the benefit of priority of Singapore patent application No. 10201408029P, filed 2 Dec. 2014, the content of which was incorporated by reference in its entirety for all purposes.

TECHNICAL FIELD

Various embodiments relate to a sensor patch and a sensing device having the sensor patch.

BACKGROUND

Intravenous (IV) cannulation is a routine procedure for most hospital patients for drug or fluid administration. Successful delivery of drugs and fluids depends on the cannula remaining in the vein at all times. Extravasation refers to the accidental leakage of IV drugs from the vein to the surrounding tissues. This can occur for a variety of reasons such as (1) incorrect placement of the cannula, (2) fragile veins (especially in infants and the elderly), (3) excessive movement from the patient resulting in the cannula being pulled out and (4) excessive pressure from the infusion pump used to infuse fluids, damaging the vein or dislodging the cannula. Extravasation begins with the drug accumulating in the subcutaneous tissue distal to the cannula, creating a bulky area. Complications related to extravasations may be quite severe and may include irritation, congestion, blistering and even necrosis of the tissue. Severe cases may result in prolonged hospital stays, cosmetic defects, functional impairment and require reconstructive surgery to repair.

Extravasation is frequently detected late when a large subcutaneous "bump" is noticed at the IV cannulation site, indicating that a large amount of infused fluid has infiltrated the surrounding tissues. This is a particular problem in the operating room with anaesthetized children, as it is often impossible to visualize the cannula site when patients are under surgical drapes. The severity of extravasation injury depends on the volume/type of drug extravasated and the time lapse before the extravasation is detected. It is important to detect extravasation early for two main reasons. Firstly, early detection will limit any potential damage to the surrounding tissues. This is of crucial importance during infusion of vesicant drugs which cause tissue destruction or irritant drugs which in turn cause pain or inflammation in the tissues. Secondly, early detection of extravasation will ensure that the drugs/fluids administered will reach the patient's intravascular space as intended, failure of which can jeopardize medical management and compromise patient care.

Currently available devices to detect extravasation are expensive, bulky, cumbersome and not for routine use. The occlusion alarms provided by conventional infusion pumps are neither sensitive nor specific enough to detect extravasation. Occlusion pressure limit cannot reliably detect extravasation especially at sites with high compliance, low flow rates, even when pump is set to low occlusion limits.

One available extravasation detector utilizes radio frequency wave (RF Wave) technology to prevent moderate to severe extravasation. It is incorporated into an injection system and stops injection when pooling of fluid is detected under the patient's skin. However, this system is expensive, cumbersome and impractical for detecting early extravasation.

An extravasation detector based on microwave radiometry has also been presented. It relies on temperature differentials in the region of accumulated fluids and is able to detect very small volumes of fluid extravasation. However, the sensor may be too sensitive, leading to frequent false alarms.

Ultrasound Doppler sensor has also been used to measure blood flow velocity in the vein for extravasation detection. If the cannula is properly sited and the contrast medium flows as desired along the vein, this will lead to an increased flow velocity in the vein.

Another available extravasation detection system, as part of a contrast injection system, comprises an electrode patch with an embedded sensor. It pauses injections if a clinically significant variation is detected and is useful only at high flow rates. It detects large volumes of extravasation and is not sensitive enough to detect early extravasation. The electrode patches need to contact with patient's skin to measure the tissue impedance when extravasation occurs.

Another device is a transducer embedded in a fixture to detect extravasation. The transducer can sense the normal force caused by skin swelling. However, it is difficult to detect shear force caused by skin stretch during low infusion rate (<10 ml) cannulation.

There is therefore an urgent clinical need for a small, portable, practical and cost-effective device to detect early extravasation, and which may trigger a warning, may be independent of rate of infusion and which can be universally applied to all patients.

SUMMARY

According to an embodiment, a sensor patch for detecting extravasation is provided. The sensor patch may include an elastic film, and at least one sensing electrode disposed on the elastic film, wherein an electrical resistance of the at least one sensing electrode is changeable in response to a force acting on the at least one sensing electrode.

According to an embodiment, a sensing device is provided. The sensing device may include a sensor patch as described herein, and a readout circuit for determining the electrical resistance of the at least one sensing electrode of the sensor patch.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which:

FIG. 5A shows the sensor patch of various embodiments with an external reader circuitry on a hand under extravasation situation, while

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may relate to non-invasive biomedical devices.

Various embodiments may provide a highly conformal sensor patch for early extravasation detection.

Various embodiments may provide a portable, practical and cost-effective sensor patch which may be universally applied to all patients to prevent extravasations injuries. Intravenous cannulation is a routine procedure for most hospital patients for drug or fluid administration. Successful delivery of drugs and fluids depends on the cannula remaining in the vein at all times. Extravasation refers to the accidental leakage of intravenous drugs from the vein to the surrounding tissues. Extravasation begins with the drug accumulating in the subcutaneous tissue distal to the cannula, creating a bulky area. Currently available devices to detect extravasation are expensive, cumbersome and not for routine use. The occlusion alarms provided by conventional infusion pumps are neither sensitive nor specific enough to detect extravasation. There is therefore an urgent clinical need for a portable, practical and cost-effective device to detect early extravasation which may be universally applied to all patients. The conformal sensor patch of various embodiments may prevent injuries in the early stage of extravasation. Skin swelling caused by extravasation may be detected through the sensor patch. The sensor patch or device of various embodiments may utilize a strain-gauge patch attached to the skin via an adhesive. Changes in skin stretch during extravasation changes the electrical impedance of the strain-gauge, which triggers an alarm. This may aid in early detection of extravasation and reduce the incidence and severity of this potentially devastating problem. To characterize the performance of patch, bench-top and ex vivo measurements were performed and discussed below.

Various embodiments may provide a sensor or a sensor patch which may employ a sensing mechanism that may detect skin stretching and/or swelling. The sensor patch may be a strain sensor. The sensor patch may provide a single (one) sensing site or multiple sensing sites. The sensor patch may be portable and/or may provide wireless operability.

The sensor patch of various embodiments may provide one or more of the following: (1) sensitive to detect small fluid of extravasation; (2) independent of rate of infusion; (3) small and portable; (4) low cost; (5) conformal sensor patch: easily attach on tissue (e.g., of a patient); (6) radio frequency (RF) wireless transmitter module; (7) without any skin contact with device/sensor patch.

Various embodiments may provide a sensor patch which may be or may include a piezoresistive strain sensor embedded into or onto an elastic film for early extravasation detection. When extravasation occurs, the swelling stretches the sensor patch, triggering an alarm to warn the clinician.

Figure 1A:
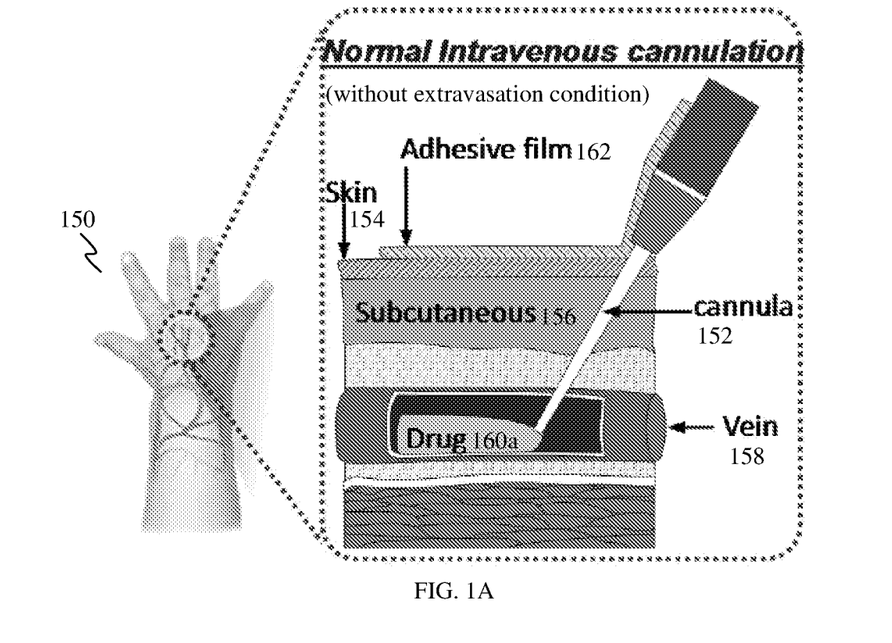
FIGS. 1A and 1B respectively show schematic diagrams of intravenous cannulation without extravasation condition and with extravasation condition.
Figure 1B:
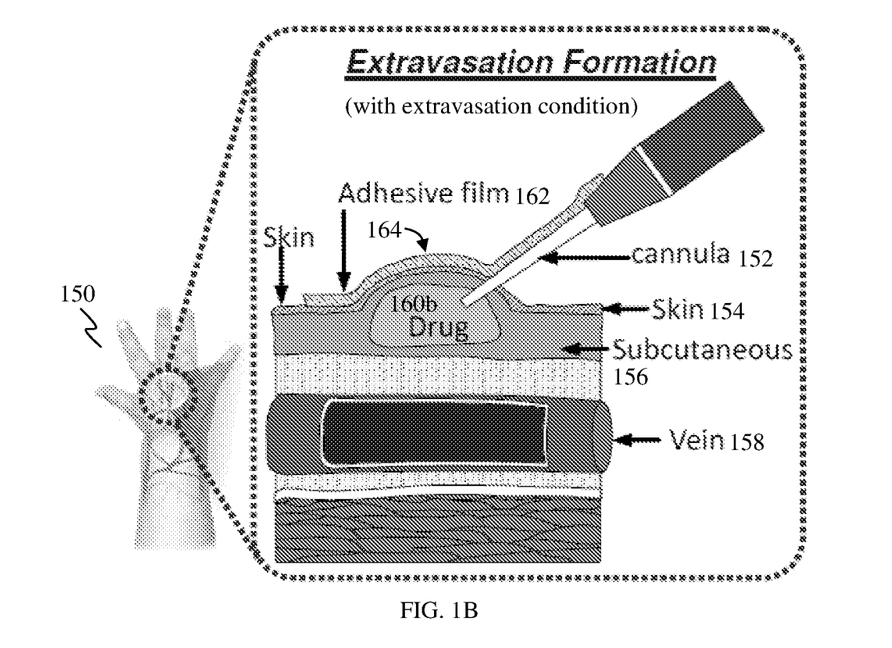

FIGS. 1A and 1B show schematic diagrams of intravenous cannulation with different conditions. Intravenous cannulation may be performed on the hand 150 of a subject or patient. FIG. 1A shows successful intravenous cannulation, without extravasation condition. A cannula 152 may be inserted or provided through the skin 154 and the subcutaneous tissue 156 of the patient. The cannula 152 refers to a tube that may be inserted into the body, for example, for the delivery or removal of fluid (e.g., drug). As shown in FIG. 1A, the cannula 152 may be inserted into the vein 158 and may remain in the vein 158 at all times and drug 160a may be injected into the vein 158. An adhesive film 162 may be used to hold or fix the cannula 152 remaining in the vein 158 to avoid the dislocation of the cannula 152. FIG. 1B shows unsuccessful intravenous cannulation, with extravasation condition. Drug 160*b* is injected into the subcutaneous tissue 156 and a bump 164 is formed below or underneath the skin 154.

The best approach to avoid extravasation injuries is careful monitoring of infusions and constant visual inspection of the cannula site. However, this may be difficult in the operating room, especially with infants and small children. When the patient is anaesthetized and under the surgical drapes, it is often impossible to visualize the cannula site. The occlusion alarms provided by infusion pumps are neither sensitive nor specific enough to detect extravasation. The current available devices to detect extravasation are expensive, cumbersome and not for routine use.

Various embodiments may provide a sensor or sensor patch (e.g., a conformal sensor patch) to address the issues of current devices. The sensor patch of various embodiments may be employed for early extravasation detection.

Figure 2A:
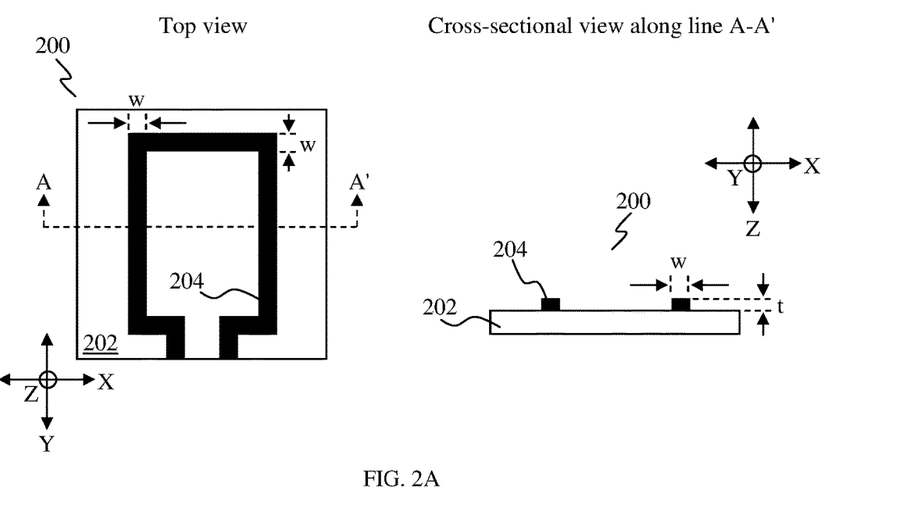
FIG. 2A shows a schematic cross-sectional view of a sensor patch, according to various embodiments.

FIG. 2A shows top and schematic cross-sectional views of a sensor patch 200, according to various embodiments. The sensor patch 200 includes an elastic film 202, and at least one sensing electrode 204 disposed on the elastic film 202, wherein an electrical resistance of the at least one sensing electrode 204 is changeable in response to a force acting on the at least one sensing electrode 204. The sensor patch 200 may be employed for detecting (early) extravasation.

In other words, a sensor patch 200 for detecting extravasation may be provided. The sensor patch 200 may include an elastic film (or elastic substrate or carrier) 202. In other words, the elastic film 202 may be made of an elastic material. The elastic film 202 may be flexible.

The sensor patch 200 may further include at least one sensing electrode (or sensing element) 204 provided or arranged on the elastic film 202. An electrical resistance (or impedance) of the at least one sensing electrode 204 may be changeable in response to a force acting or exerted on the at least one sensing electrode 204. This may mean that the at least one sensing electrode 204 may be configured to exhibit a change in electrical resistance in response to a force acting on or exerted on the at least one sensing electrode 204. The force may also act on the elastic film 202. The at least one sensing electrode 204 may not or does not need contact with a skin surface for extravasation detection.

The at least one sensing electrode 204 may define a sensing area (or detecting area) of the sensor patch 200. The sensing area may be defined by the shape and/or size of the at least one sensing electrode 204. For example, the area of the sensor patch 200 provided with the at least one sensing electrode 204 may correspond to the sensing area.

In various embodiments, the force acting on the at least one sensing electrode 204 may cause a change in at least one dimension (e.g., length and/or width) of the at least one sensing electrode 204, thereby causing a change in the electrical resistance of the at least one sensing electrode 204.

In various embodiments, where the sensor patch 200 with the at least one sensing electrode 204 is positioned on a surface, a change in a contour (or topography or shape) of the surface, e.g., resulting in a bump, may cause a force to act on or to be exerted on the at least one sensing electrode 204. As a result, the electrical resistance of the at least one sensing electrode 204 may change. Changes in the contour of the surface may be conveyed by the elastic film 202 to the at least one sensing electrode 204.

As a non-limiting example, the sensor patch 200 with the at least one sensing electrode 204 may be positioned on a skin surface of a subject (or patient), over a cannulation site. In the event that extravasation occurs, the contour (or topography or shape) of the skin surface over the cannulation site may change (e.g., resulting in a bump), and the at least one sensing electrode 204 may experience a force acting on it, causing a change in at least one dimension (e.g., length and/or width) of the at least one sensing electrode 204, thereby changing its electrical resistance. For example, when a protrusion (e.g., a bump) occurs in the skin or skin surface, the electrical resistance of the at least one sensing electrode 204 may increase. When extravasation occurs, changes in the skin or skin surface, for example, swelling, may stretch the sensor patch 200. This may result in a change in the electrical resistance of the at least one sensing electrode 204, due to a change in at least one dimension (e.g., length and/or width and/or thickness) of the at least one sensing electrode 204, as a result of stretching of the at least one sensing electrode 204. Therefore, skin swelling caused by extravasation may be detected through the sensor patch 200.

In various embodiments, the elastic film 202 may be adapted to conform to a contour (or topography or shape) of a surface on which the sensor patch 200 is positioned. This may mean that the sensor patch 200 may be a conformal sensor patch.

In various embodiments, the sensor patch 200 may be stretchable. This may mean that the elastic film 202 may be stretchable. Correspondingly, the at least one sensing electrode 204 may also be stretchable. The elastic film 202 and the at least one sensing electrode 204 of the sensor patch 200 may be stretchable for sensing extravasation bump formation. In various embodiments, the elastic film 202 may be made of an elastic and stretchable material.

In various embodiments, the elastic film 202 may be a flexible elastic film or substrate which may be stretchable, and the at least one sensing electrode 204 may be a stretchable sensing electrode or sensing element disposed on the flexible elastic film 202.

In various embodiments, the at least one sensing electrode 204 may include a strain gauge. This may mean that the sensor patch 200 may be a strain-gauge sensor patch.

In various embodiments, the at least one sensing electrode 204 may include a piezoresistive material. This may mean that the at least one sensing electrode 204 may exhibit piezoresistive effect. In this way, a piezoresistive type sensor patch 200 for extravasation detection may be provided.

In various embodiments, the sensor patch 200 may further include an adhesive layer provided on one side of the elastic film 202. For example, the adhesive layer may be provided (e.g., directly) on a surface (e.g., bottom surface) of the elastic film 202. The adhesive layer may provide an adhesive surface to be placed over a skin surface, without any strap, arm band or housing, to secure the sensor patch 200 on the body of a subject or patient.

In various embodiments, the at least one sensing electrode 204 may be disposed on another side of the elastic film 202 opposite to the one side of the elastic film 202. For example, the at least one sensing electrode 204 may be provided (e.g., directly) on another surface (e.g., top surface) of the elastic film 202 opposite to the surface of the elastic film 202 on which the adhesive layer may be provided.

In various embodiments, the at least one sensing electrode 204 may be stretchable and patterned on the stretchable, adhesive elastic film 202, which may be reused at the same site before peeling the sensor patch 200 from the skin of a subject.

In various embodiments, the sensor patch 200 may further include at least one pair of bonding pads electrically coupled to the at least one sensing electrode 204. The at least one pair of bonding pads may be electrically coupled or connected to a readout circuit (e.g., an external readout circuit) for determining the electrical resistance or the change of the electrical resistance of the at least one sensing electrode 204. In this way, the at least one sensing electrode 204 may be electrically coupled to a readout circuit via the at least one pair of bonding pads. In various embodiments, a respective pair of bonding pads may be electrically coupled to a respective (one) sensing electrode 204.

In various embodiments, the at least one sensing electrode 204 may be printed on the elastic film 202. The at least one sensing electrode 204 may be printed directly on the elastic film 202 without any glue or adhesive between the at least one sensing electrode 204 and the elastic film 202. In various embodiments, the at least one sensing electrode 204 may be patterned on the elastic film 202.

In various embodiments, the at least one sensing electrode 204 may be formed into an arrangement having at least one of a linear pattern (as shown in FIG. 2A), a curved pattern, a meander pattern, a zig zag pattern or a spiral pattern.

In the context of various embodiments, the elastic film 202 may include a polymer. The polymer for the elastic film 202 may include polyethylene, silicone, urethane polymer, acrylate resin, Rayon, parylene, polyimide etc.

In the context of various embodiments, the at least one sensing electrode 204 may include at least one of metal, liquid metal alloy or conductive polymer.

Non-limiting examples of metals that may be used for the at least one sensing electrode 204 may include titanium (Ti), gold (Au), nickel (Ni), copper (Cu), chromium (Cr), aluminium (Al), indium (In), platinum (Pt), silver (Ag) and tin (Sn).

Non-limiting examples of liquid metal alloys that may be used for the at least one sensing electrode 204 may include Galinstan which may have a composition including gallium, indium, and tin.

Conductive polymers or intrinsically conducting polymers that may be used for the at least one sensing electrode 204 may include organic polymers that conduct electricity. The compounds used may have metallic conductivity or may be semiconductors, such as silver, graphite, copper powder, carbon black or carbon nanotubes, etc.

In various embodiments, the at least one sensing electrode 204 may be formed as a single layer or as a stacked layer arrangement of different layers. For example, the at least one sensing electrode 204 may be a single metal layer or a double layer arrangement having different metals in different layers.

In the context of various embodiments, a width, w, of the at least one sensing electrode 204 may be between about 0.5 mm and about 10 mm, for example, between about 0.5 mm and about 5 mm, between about 0.5 mm and about 2 mm, between about 2 mm and about 10 mm, between about 2 mm and about 5 mm, between about 5 mm and about 10 mm. The width, w, of the at least one sensing electrode 204 may be at least substantially uniform throughout the at least one sensing electrode 204.

In the context of various embodiments, a thickness, t, of the at least one sensing electrode 204 may be about 0.2 μm or less (i.e., ≤0.2 μm), e.g., ≤0.15 μm, ≤0.1 μm, or ≤0.05 μm. The thickness, t, of the at least one sensing electrode 204 may be at least substantially uniform throughout the at least one sensing electrode 204. The thickness of the at least one sensing electrode 204 may be a less than 0.2 μm metal thin film to detect extravasation with high sensitivity. The very thin (0.2 μm) metal layer may be printed on the elastic (stretchable) film 202.

For example, the at least one sensing electrode 204 may be a metal layer of a thickness of about 0.2 μm. As a non-limiting example, a very thin (0.2 μm) metal layer (as the sensing electrode 204) printed on an elastic (stretchable) film 202 may have an average (N=9) resistance change of about 31 Ω/ml of saline infusion without the use of additional bridge network. In a general case, 2 ml of infusion may be considered as early extravasation. The sensor patch 200 of various embodiments may be more sensitive and may have a high signal to noise ratio (e.g., >4.1), which may detect slight skin swelling and tension caused by an early extravasation injury.

In various embodiments, the sensitivity of the sensor patch 200 may be determined by the width, w, and/or the thickness, t, of the at least one sensing electrode 204.

In the context of various embodiments, a length of the at least one sensing electrode 204 may be between about 5 cm and about 100 cm, for example, between about 5 cm and about 50 cm, between about 5 cm and about 20 cm, between about 10 cm and about 50 cm, between about 20 cm and about 100 cm, between about 50 cm and about 100 cm, or between about 20 cm and about 40 cm.

In various embodiments, the electrical resistance of the at least one sensing electrode 204 may be changeable in response to at least one of a normal force (e.g., due to skin swelling) or a shear force (e.g., due to skin stretching or tension) acting on the at least one sensing electrode 204.

In various embodiments, the electrical resistance of the at least one sensing electrode 204 may be changeable in response to one or more forces acting on the at least one sensing electrode 204 in x-, y- and z-directions of a three-dimensional Cartesian coordinate system. The electrical resistance of the at least one sensing electrode 204 may be changeable in response to a force acting on the at least one sensing electrode 204 in the x-direction, a force acting on the at least one sensing electrode 204 in the y-direction, and a force acting on the at least one sensing electrode 204 in the z-direction, as well as a force having force components acting on the at least one sensing electrode 204 in at least two directions of the x-, y- and z-directions. This may mean that the sensor patch 200 having the at least one sensing electrode 204 may be able to detect skin deformation (e.g., tension/swelling) in 3 axes (x-y-z directions). Therefore, the sensor patch 200 may detect skin tension and/or skin swelling, in the x-y-z directions, caused by (early) extravasation injury.

In various embodiments, the sensor patch 200 may include a single (one) sensing electrode 204.

In various embodiments, the sensor patch 200 may include a plurality of sensing electrodes 204, e.g., two sensing electrodes, three sensing electrodes or any higher number of sensing electrodes. The plurality of sensing electrodes 204 may be electrically isolated from each other.

In various embodiments, the sensor patch 200 may be a planar sensor patch 200.

Figure 2B:
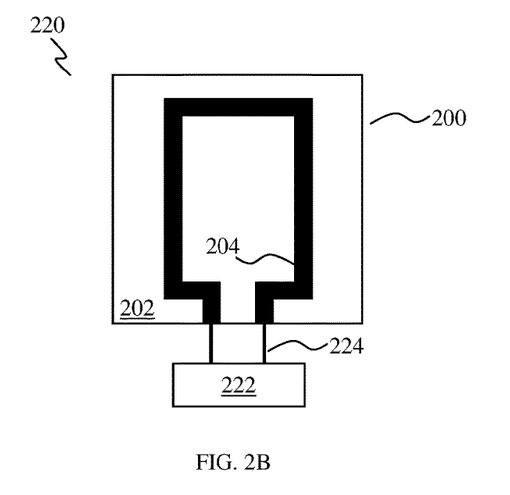
FIG. 2B shows a schematic cross-sectional view of a sensing device, according to various embodiments.

FIG. 2B shows a schematic cross-sectional view of a sensing device 220, according to various embodiments. The sensing device 220 includes the sensing patch 200 as described above, and a readout circuit 222 for determining the electrical resistance of the at least one sensing electrode 204 of the sensor patch 200. The readout circuit 222 may determine the absolute value of the electrical resistance of the at least one sensing electrode 204 and/or the change in the electrical resistance of the at least one sensing electrode 204. The readout circuit 222 may be electrically coupled to the at least one sensing electrode 204, for example via an electrical interconnection (e.g., wire or cable) 224. The readout circuit 222 may be external to the sensor patch 200. The readout circuit 222 may be a microprocessor.

In the context of various embodiments, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a 'circuit' in accordance with an alternative embodiment.

In various embodiments, the sensing device 220 may further include at least one of a visual means (e.g., a visual alert LED) or an audio output means. The audio output means may be electrically coupled to the readout circuit 222. The audio output means may be an alarm or a buzzer. As a non-limiting example, the audio output means may be activated to provide an audio signal, for example, when the electrical resistance of the at least one sensing electrode 204 is equal to or more than a first predetermined threshold level, or when a change (from an initial electrical resistance value) in the electrical resistance of the at least one sensing electrode 204 is equal to or more than a second predetermined threshold level. This may provide a warning or an indication to a clinician or a doctor that there may be extravasation.

In various embodiments, the sensing device 220 may further include a radio frequency (RF) wireless module electrically coupled to the readout circuit 222. The RF wireless module may include at least one of a transmitter or a receiver. As a non-limiting example, the RF wireless module may transmit information or data obtained by the readout circuit 222 wirelessly to a remote device or processor, or to receive a signal wirelessly from a remote device or processor to activate the sensor device 220 to perform sensing.

Figure 3:
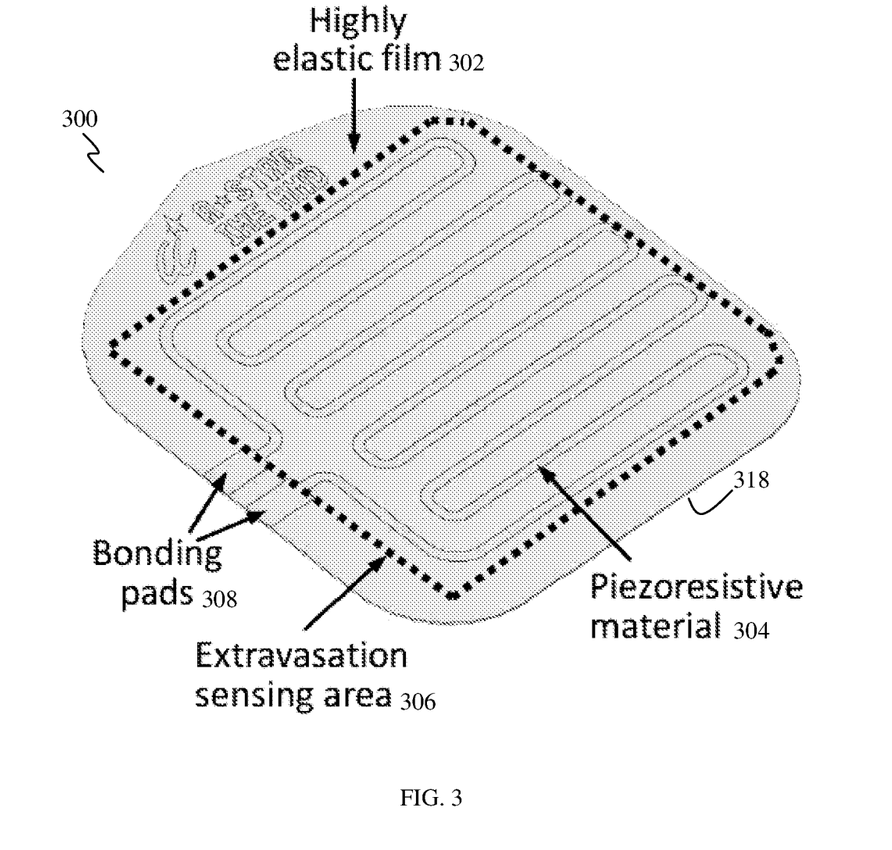
FIG. 3 shows a schematic perspective view of a sensor patch, according to various embodiments.

FIG. 3 shows a schematic perspective view of a sensor patch 300, according to various embodiments. The sensor patch 300 may address the issues of current devices which are expensive, cumbersome and unsuitable for routine use.

The (conformal) sensor patch 300 may include an elastic film 302 and a sensing electrode 304 made of a piezoresistive material provided on the elastic film 302. Therefore, the elastic film 302 may act as a substrate for the sensing electrode 304. The sensing electrode 304 may be patterned on the elastic film 302. The sensing electrode 304 may be provided on an upper surface of the elastic film 302. The sensing electrode 304 may be arranged in a meander pattern.

The sensing electrode 304 of piezoresistive material may act as a strain sensing element, and may be used, for example, for sensing tissue skin stretch. The elastic film 302 may convey or conduct tissue skin tension to the piezoresistive sensor 304. The electrical resistance of the sensing electrode 304 of piezoresistive material may be changeable or variable, in response to a force acting on it, for example, as a result of skin stretching. The material of the sensing electrode 304 may be chosen as metal and/or conductive polymer.

A sensing area (e.g., extravasation sensing area) 306 may be defined by the sensing electrode 304, for example, by the arrangement, pattern or shape of the sensing electrode 304. The sensing area 306 may be defined by a single sensing electrode 304, as shown in FIG. 3, or by a multi-electrode arrangement (i.e., plurality of sensing electrodes).

A pair of bonding pads 308 may be provided electrically coupled to the sensing electrode 304. For example, one bonding pad 308 may be connected to one end of the sensing electrode 304 while another bonding pad 308 may be connected to another (opposite) end of the sensing electrode 304. The bonding pads 308 of the patch 300 may be used for interconnection with an external reader circuitry (not shown).

While not clearly shown, an adhesive layer 318 may be provided on one side of the elastic film 302, for example, on the bottom surface of the sensor patch 300. The adhesive layer 318 may be used to conformally attach the sensor patch 300 on the skin of a subject or patient.

As described above, the sensor patch 300 may be a conformal piezoresistive strain sensor patch.

Figure 4A:
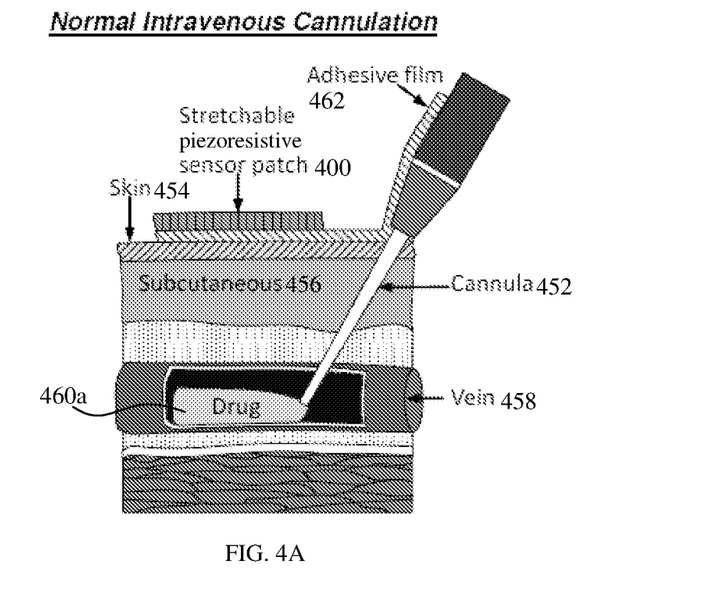
FIGS. 4A and 4B show schematic diagrams of the working principle of the sensor patch, according to various embodiments.
Figure 4B:
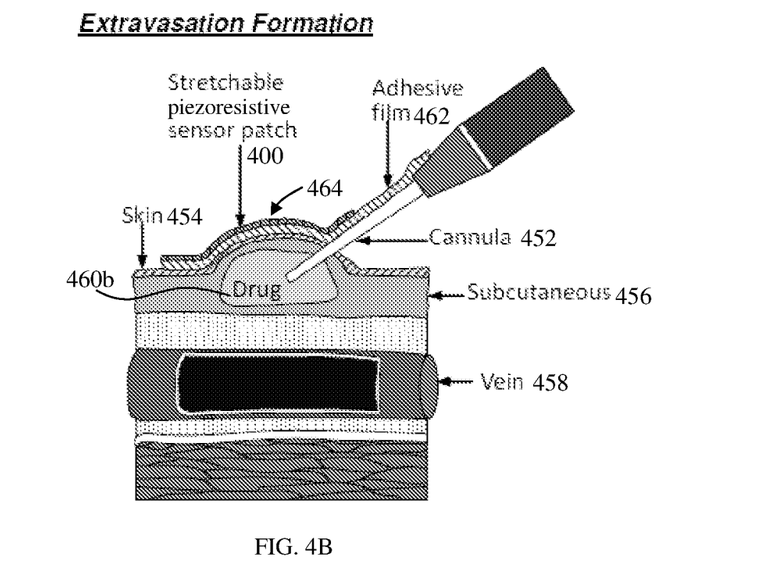

FIGS. 4A and 4B show schematic diagrams of the working principle of the sensor patch 400, according to various embodiments. The sensor patch 400 may be as described in the context of the sensor patch 200 (FIG. 2A), 300 (FIG. 3). FIG. 4A shows a schematic diagram of normal intravenous cannulation, without extravasation condition. A cannula 452 may be inserted or provided through the skin 454 and the subcutaneous tissue 456 of a subject or patient. As shown in FIG. 4A, the cannula 452 may be inserted into the vein 458 and may remain in the vein 458 at all times and drug 460a may be injected into the vein 458. An adhesive film 462 may be used to hold or fix the cannula 452 remaining in the vein 458 to avoid the dislocation of the cannula 452. The sensor patch 400 of various embodiments may be provided or attached to the adhesive film 462.

FIG. 4B shows an intravenous cannulation with extravasation formation. Drug 460b is injected into the subcutaneous tissue 456 and a bump 464 is formed below or underneath the skin 454. The sensor patch 400 on the adhesive film 462 may change its shape from an initial planar state into a state that at least substantially corresponds to that of the bump 464. The sensor patch 400, with the elastic film (e.g., 302) and the sensing electrode (e.g., 304), may be deformed or stretched as a result of the formation of the bump 464 beneath the sensor patch 400, thereby generating at least one force acting on the sensing electrode. The resistance or impedance value of the sensing electrode may increase when the bump 464 is formed in the subcutaneous tissue 456 due to extravasation. When extravasation occurs, the swelling or bump 464 stretches the sensor patch 400, which may trigger an alarm to warn a clinician about the condition of the patient.

Figure 5A:
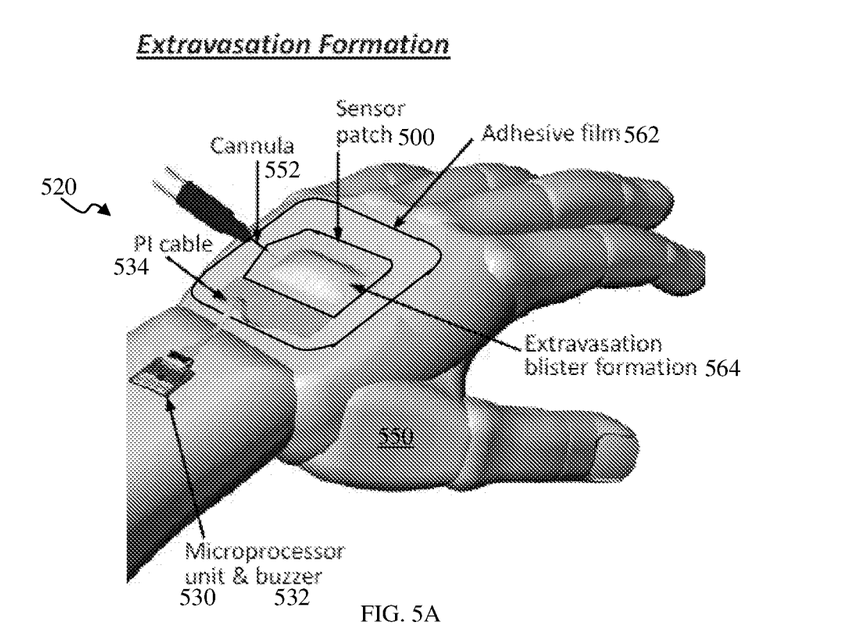
Figure 5B:
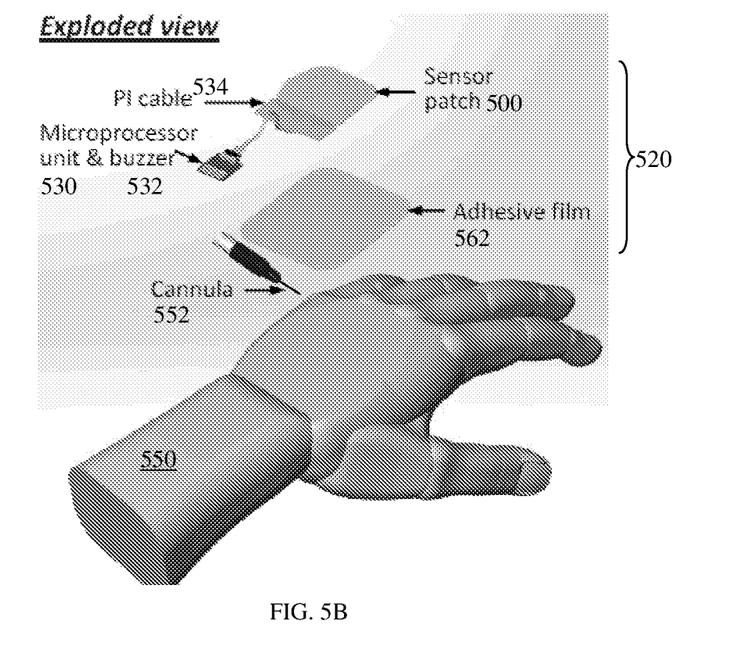
FIG. 5B shows an exploded view of the sensor patch.

FIG. 5A shows the sensor patch 500 of various embodiments with an external reader circuitry on a hand 550 under extravasation situation (with formation of extravasation blister 564), while FIG. 5B shows an exploded view of the sensor patch 500 for extravasation detection. The sensor patch 500 may be as described in the context of the sensor patch 200 (FIG. 2A), 300 (FIG. 3). The sensor patch 500 may be part of a sensing device 520, which may be an extravasation detection system.

The conformal sensor patch 500 may be directly attached on a conventional adhesive film 562 of intravenous cannulation to avoid human skin contact with the sensor patch 500. The advantages without skin contact of the sensor patch 500 may include less biocompatibility consideration of medical device and a faster regulatory approval period.

The sensing device 520 may include a readout circuit, such as an external reader circuit, which may be a microprocessor unit 530. The sensing device 520 may also include an audio output means, for example, a buzzer 532. The buzzer 532 may be electrically coupled to or may be part of the microprocessor unit 530. The microprocessor unit 530 may be electrically connected to the sensor patch 500, more specifically to the sensing electrode of the sensor patch 500, via a polyimide (PI) cable 534 as shown in FIGS. 5A and 5B, or via an insulated electrical wire.

Fabrication and packaging of the sensor patch of various embodiments will now be described by way of the following non-limiting example with reference to FIGS. 6A to 6E illustrating the fabrication process of the sensor patch.

FIGS. 6A to 6E show, as cross-sectional views, various processing stages of a method for fabricating a sensor patch, according to various embodiments, illustrating the fabrication process flow 660 for the sensor patch.

Figure 6A:
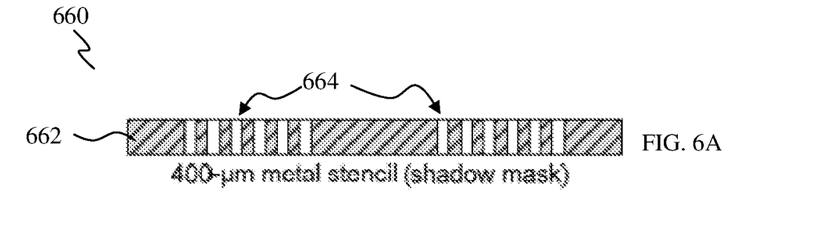
FIGS. 6A to 6E show, as cross-sectional views, various processing stages of a method for fabricating a sensor patch, according to various embodiments.
Figure 6B:
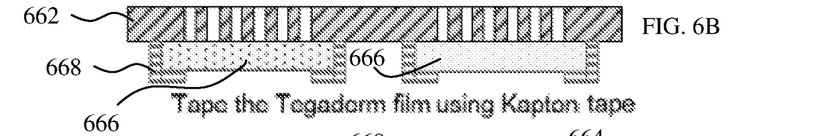
Figure 6C:
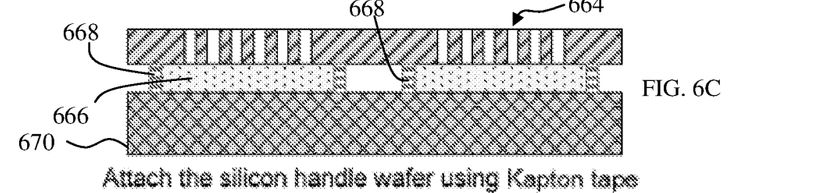
Figure 6D:
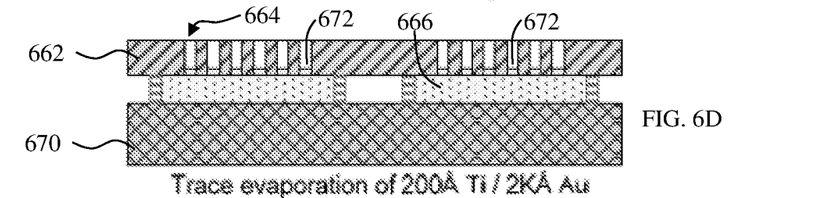
Figure 6E:
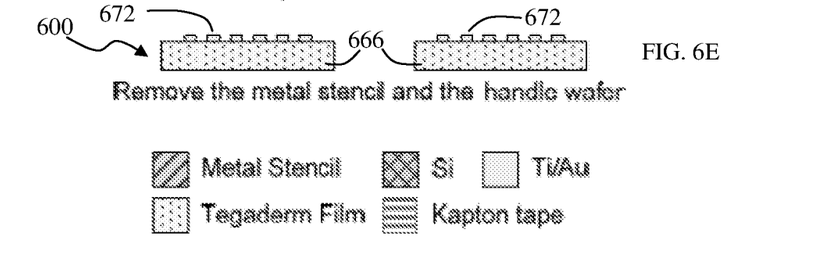

As shown in FIG. 6A, first of all, a 400-μm stainless stencil 662 may be fabricated by laser micromachining as a shadow mask. As a result, a plurality of apertures, for example, through holes or channels 664, may be defined through the stencil 662. Adhesive films (e.g., Tegaderm film) 666 may be attached on the stencil plate 662 using Kapton tape 668, as shown in FIG. 6B. Then, a carrier or support substrate 670, for example, an eight-inch silicon (Si) wafer, may be used as a carrier wafer for the subsequent metal evaporation process, and the adhesive films 666 with the stencil 662 may be attached on or to the (Si) carrier wafer 670, as illustrated in FIG. 6C. Referring to FIG. 6D, one or more metal(s) 672, for example, titanium/gold (Ti/Au) (thickness 200 Å/2000 Å), may be evaporated, via the apertures 664 of the stencil 662, on the adhesive films 666 as the sensing electrodes on the adhesive films 666. As shown in FIG. 6E, after release of the carrier wafer 670 and the stencil 662, sensor patches 600 (with sensing electrode(s) 672) may be obtained. It should be appreciated that while FIGS. 6A to 6E illustrate the fabrication of two sensor patches 600, any number of sensor patches may be (simultaneously) formed using the stencil 662.

Here, one of many technologies that may be employed to form the sensor patch of various embodiments is presented, and it should be appreciated that the manufacturing process or techniques of the sensor patch may be changed, for example, depending on the fabrication cost and/or quantities of production.

FIGS. 7A to 7D show top views of the fabricated sensor patches 700a, 700b, 700c, 700d of various embodiments, for example, for early extravasation detection.

Figure 7A:
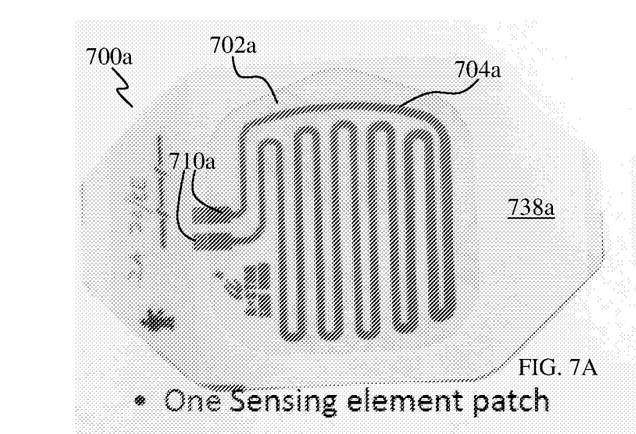
FIGS. 7A to 7D show top views of the fabricated sensor patches of various embodiments.

FIG. 7A shows a one-sensing element sensor patch 700a having a single sensing electrode 704a provided on an elastic film 702a. The sensing electrode 704a may be formed in an arrangement having a combination of linear pattern, curved pattern and meander pattern. A pair of bonding pads 710a may be provided electrically coupled to the sensing electrode 704a.

Figure 7B:
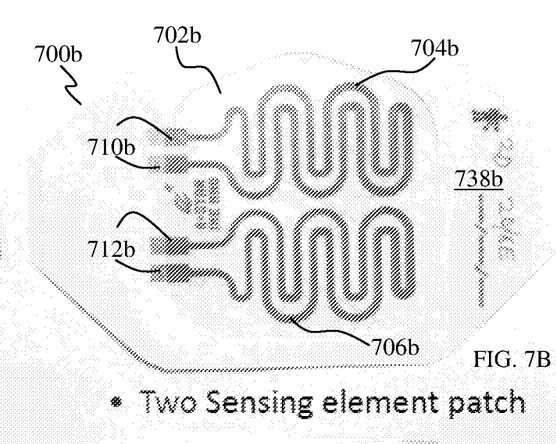

FIG. 7B shows a two-sensing element sensor patch 700b having a first sensing electrode 704b and a second sensing electrode 706b provided on an elastic film 702b. Each of the first sensing electrode 704b and the second sensing electrode 706b may be formed in an arrangement having a combination of linear pattern, curved pattern and meander pattern. A first pair of bonding pads 710b may be provided electrically coupled to the first sensing electrode 704b and a second pair of bonding pads 712b may be provided electrically coupled to the second sensing electrode 706b.

Figure 7C:
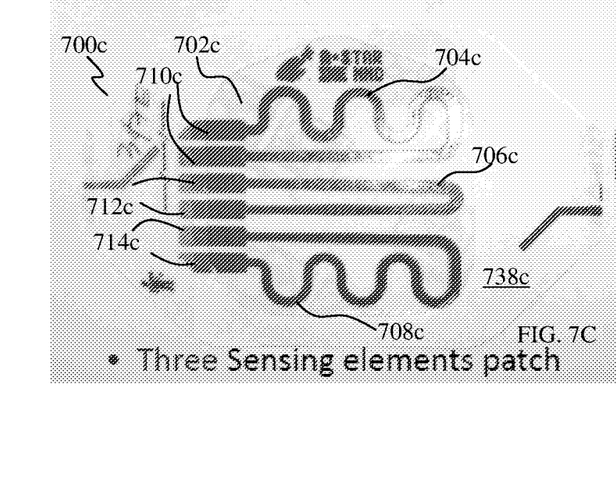

FIG. 7C shows a three-sensing element sensor patch 700c having a first sensing electrode 704c, a second sensing electrode 706c and a third sensing electrode 708c provided on an elastic film 702c. Each of the first sensing electrode 704c and the third sensing electrode 708c may be formed in an arrangement having a combination of linear pattern, curved pattern and meander pattern, while the second sensing electrode 706c may be formed in an arrangement having a combination of linear pattern and curved pattern. A first pair of bonding pads 710c may be provided electrically coupled to the first sensing electrode 704c, a second pair of bonding pads 712c may be provided electrically coupled to the second sensing electrode 706c and a third pair of bonding pads 714c may be provided electrically coupled to the third sensing electrode 708c.

Figure 7D:
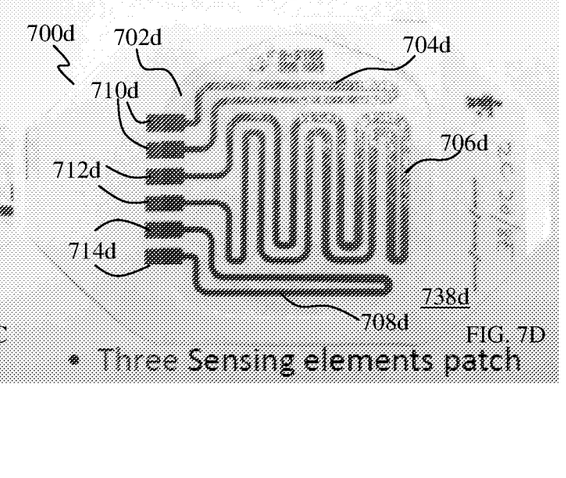

FIG. 7D shows a three-sensing element sensor patch 700d having a first sensing electrode 704d, a second sensing electrode 706d and a third sensing electrode 708d provided on an elastic film 702d. Each of the first sensing electrode 704d and the third sensing electrode 708d may be formed in an arrangement having a combination of linear pattern and curved pattern, while the second sensing electrode 706d may be formed in an arrangement having a combination of linear pattern, curved pattern and meander pattern. A first pair of bonding pads 710d may be provided electrically coupled to the first sensing electrode 704d, a second pair of bonding pads 712d may be provided electrically coupled to the second sensing electrode 706d and a third pair of bonding pads 714d may be provided electrically coupled to the third sensing electrode 708d.

Each sensor patch 700a, 700b, 700c, 700d may be provided with covering or protective layers 738a, 738b, 738c, 738d on the bottom and top surfaces of the elastic film 702a, 702b, 702c, 702c except where the sensing electrodes 704a, 704b, 706b, 704c, 706c, 708c, 704d, 706d, 708d are arranged on the top surfaces of the elastic film 702a, 702b, 702c, 702c, for example, for packaging purposes, prior to use.

Figure 8:
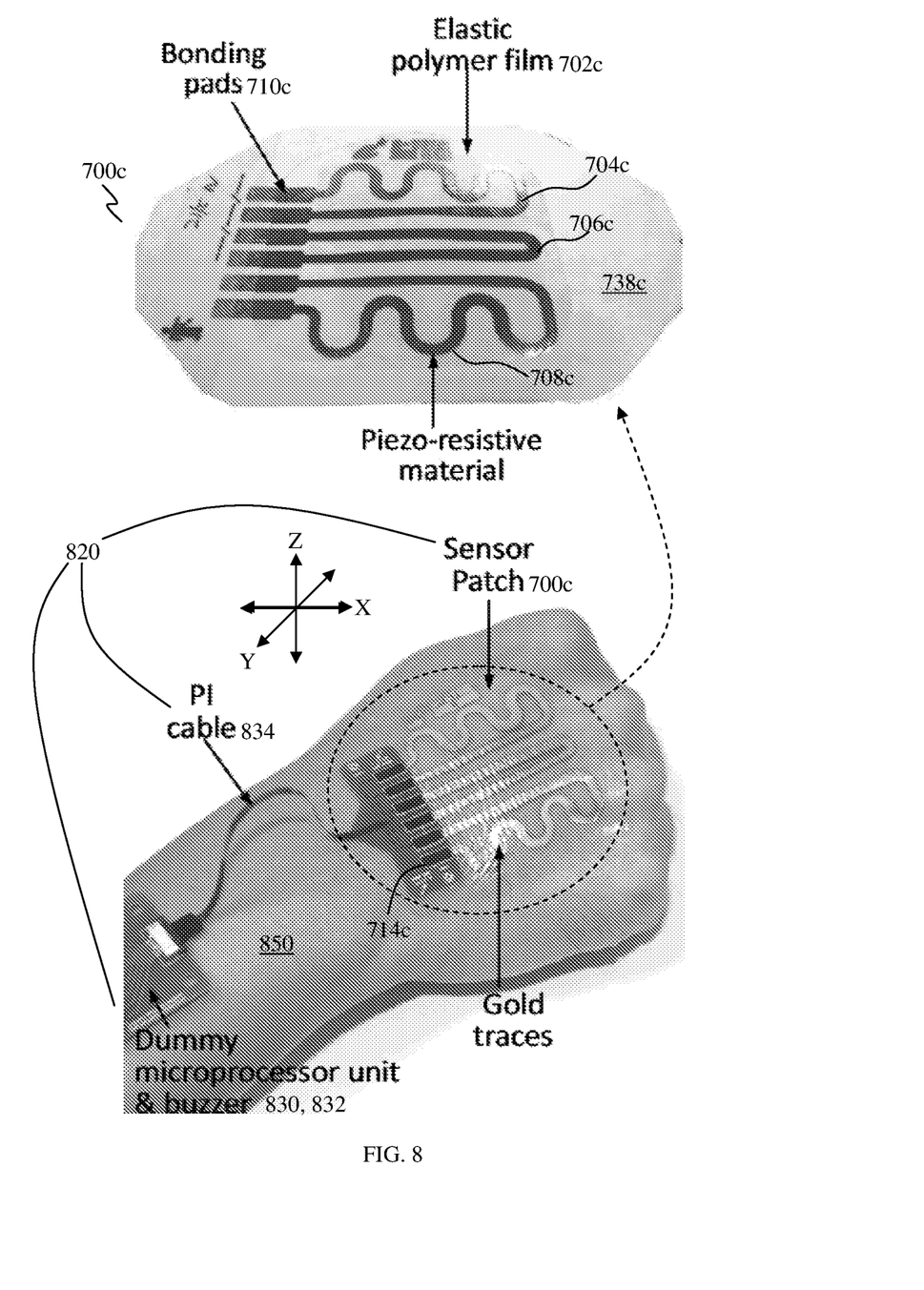
FIG. 8 shows a sensing device attached on a hand of a subject, according to various embodiments.

FIG. 8 shows a sensing device (or sensor patch system) 820 attached on a hand 850 of a subject, according to various embodiments. The sensing device 820 includes the sensor patch 700c which may include gold sensing electrodes 704c, 706c, 708c on an elastic polymer film 702c. The sensing electrodes 704c, 706c, 708c may be electrically coupled, via a PI cable 834, to a microprocessor unit 830 and a buzzer 832.

The sensor patch of various embodiments as described herein, including the sensor patch 700c illustrated in FIG. 8, may be able to detect skin deformation (e.g., tension and/or swelling) in 3 axes, such as the x-y-z directions (e.g., corresponding to a three-dimensional Cartesian coordinate system) illustrated in FIG. 8. As a non-limiting example, the z-direction may be defined normal to the sensor patch (e.g., 700c), while the x-direction and the y-direction may be orthogonal or perpendicular to the z-direction. This may mean that the x-direction and the y-direction may be along the plane of the sensor patch (e.g., 700c). A normal force or a normal force component acting on the sensor patch (e.g., 700c) or a sensing electrode (e.g., 704c, 706c, 708c), for example due to skin swelling, may be in the z-direction. A shear force or a shear force component acting on the sensor patch (e.g., 700c) or a sensing electrode (e.g., 704c, 706c, 708c), for example due to skin stretching or tension, may be in the x-direction and/or the y-direction. Therefore, skin swelling and/or skin tension detection may be carried out in the x-y-z directions through the adhesive sensor patch of various embodiments for early extravasation, without the use of any strap or belt.

Figure 9A:
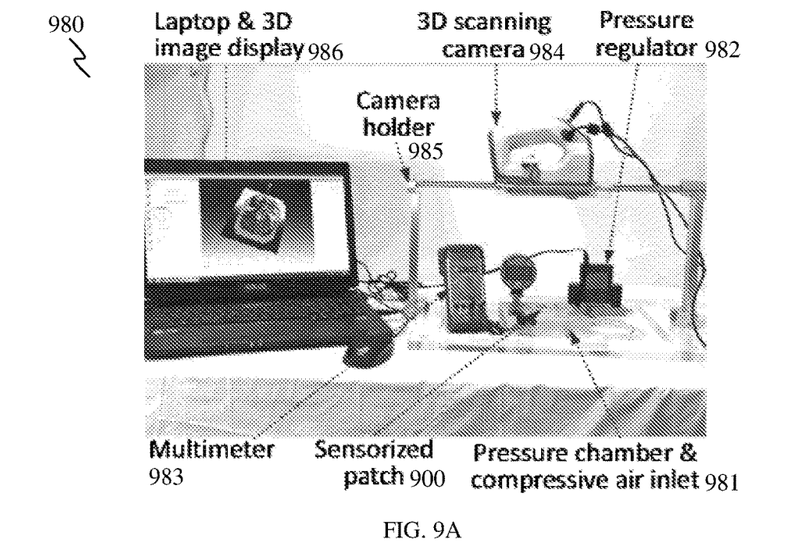
FIG. 9A shows a setup for bench-top test measurement and FIG. 9B shows a plot of the bench-top measurement results.

In order to characterize the fabricated sensor patches, a bench-top test was executed. FIG. 9A shows the bench-top test setup 980 that may be used. A fabricated sensor patch 900 of various embodiments may be attached on a customized aluminum pressure chamber jig 981 having a compressive air inlet. Compressive air may be applied into the circular hole (inlet) of the pressure chamber jig 981 to simulate bump formation due to extravasation. A pressure regulator 982 may be used to control the pressure of the compressive air applied to the jig 981. The applied pressure and the size of the customized chamber 981 were applied/designed based on the intravenous cannulation (10 ml) for the ex vivo test to be described below.

The resistance of the sensing electrode on the patch 900 may be recorded by a multimeter 983 and the formed bump height of the sensor patch 900 may be measured by a three-dimensional (3D) scanning camera 984 positioned above the sensor patch 900 via a camera holder 985. The scanned profile of the sensor patch 900 may be real-time shown on a laptop 986.

Figure 9B:
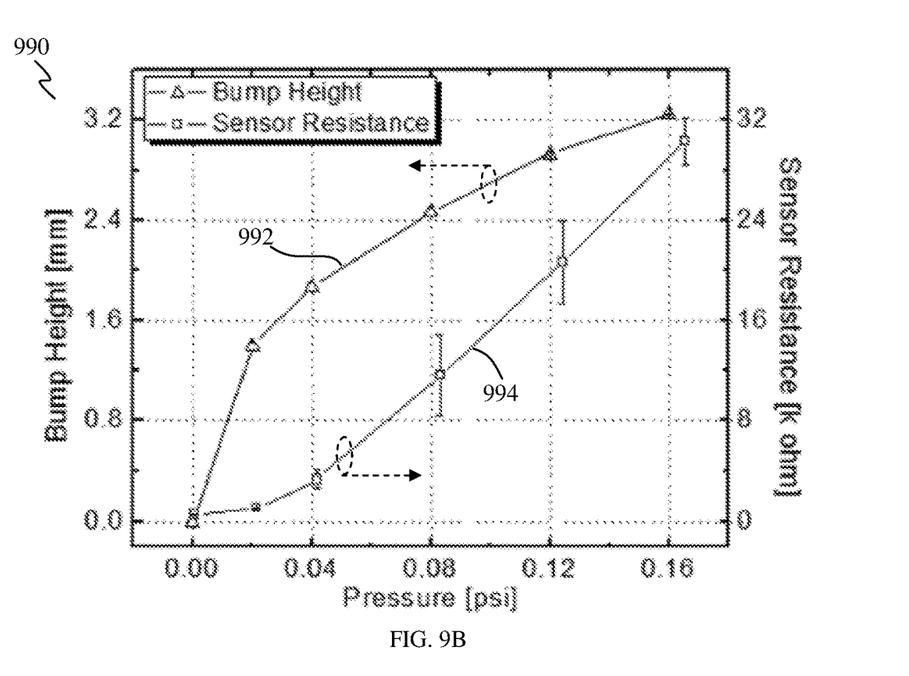

FIG. 9B shows a plot 990 of the bench-top measurement results of the fabricated sensor patch 900. As the height (see result 992) of the bump that is formed increases, the resistance (see result 994) of the sensing electrode of the sensor patch 900 on the bump also increases.

Figures 10A, 10B:
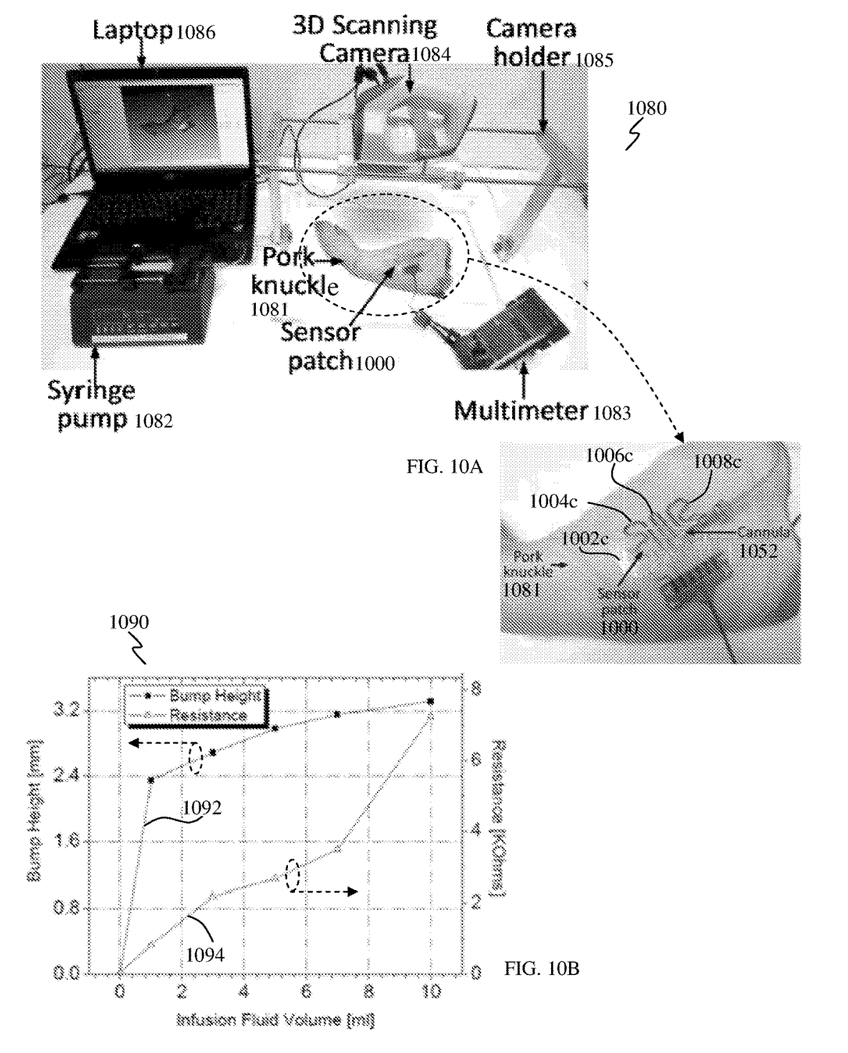
FIG. 10A shows a setup for ex vivo test measurement and FIG. 10B shows a plot of the ex vivo measurement results.

An ex vivo test was also conducted to evaluate the sensor patch of various embodiments. FIG. 10A shows the ex vivo test setup 1080 that may be used for the sensor patch 1000, which may be attached on a pork knuckle 1081. The sensor patch 1000 may include three sensing electrodes 1004c, 1006c, 1008c on an elastic film 1002c that may be attached to the pork knuckle 1081. A cannula 1052 may be inserted into the pork knuckle 1081, under the sensor patch 1000. A blue contrast solution may be injected into the subcutaneous tissue of the pork knuckle 1081 using the cannula needle 1052 to simulate the contrast solution accumulating in the tissue. The infusion rate of the contrast solution may be controlled by a syringe pump 1082. The infusion rate of the contrast solution may be fixed at about 50 ml/hr and a 10 ml contrast solution was injected into the tissue of the pork knuckle 1081. The resistance of the sensing electrodes 1004c, 1006c, 1008c and the height of the formed bump may be measured by a multimeter 1083 and a three-dimensional (3D) scanning camera 1084, respectively. The camera 1084 may be positioned above the sensor patch 1000 via a camera holder 1085. The results of the measurement may be shown on a laptop 1086.

FIG. 10B shows a plot 1090 of the ex vivo measurement results of the fabricated sensor patch 1000. As the height (see result 1092) of the bump that is formed increases, the resistance (see result 1094) of the sensing electrode (e.g., 1004c, 1006c, 1008c) of the sensor patch 1000 on the bump also increases. Based on the measurement results, the fabricated patch 1000 may be able to detect very small volume (<5 ml) contrast in subcutaneous tissue when extravasation occurs.

Various embodiments may provide a conformal sensor patch which may be universally applied to all patients to prevent or at least minimise extravasations injuries. The conformal sensor patch may be directly attached on the conventional adhesive film of intravenous cannulation to avoid patient's skin contact with the sensor patch. The advantages without skin contact of the sensor patch are less biocompatibility consideration of medical devices and a faster regulatory approval period. The sensing electrode material, which may be metal or conductive polymer, is embedded in an elastic film of the sensor patch. Extravasation detecting area may be defined by the shape and/or size of one or more sensing electrode(s). Skin swelling caused by extravasation may be detected through the sensor patch. To characterize the performance of patch, bench-top and ex vivo were performed and discussed above. Based on the measurement result, the fabricated patch of various embodiments may detect very small volume (<5 ml) contrast in subcutaneous tissue when extravasation occurs.

As described above, various embodiments may provide a conformal elastic (sensor) patch with high sensitivity or high sensitive sensing electrode for early extravasation detection (e.g., <7 ml, e.g., <5 ml). The sensor patch may be a piezoresistive type strain sensor patch for extravasation detection. The sensor patch may include an elastic film and the piezoresistive material (e.g., metal or conductive polymer) may be embedded in the elastic film. The sensing area of the sensor patch may be defined by one (single) sensing electrode (e.g., as one big area) or a multi-electrode arrangement (i.e., multiple sensing electrodes) (e.g., as many specific small areas). The sensing electrode(s) and the elastic substrate (or elastic film) of the sensor patch may be stretchable during or when there is skin tension and/or swelling. Tissue blistering (e.g., obvious bump) or swelling (not obvious bump), representative of normal force and shear force, may be detected by the conformal sensor patch, independent of rate of infusion. The sensor patch of various embodiments may be more sensitive compared to conventional devices and may detect slight skin tension and swelling (e.g., in the x-y-z directions) caused by early extravasation injury accurately.

The sensor patch of various embodiments may be used or provided onto: (1) an existing IV cannulation adhesive film (such as Tegaderm film or other adhesive films), or (2) directly on the (human) skin over the cannulation site. The conformal sensor patch may be directly attached on the conventional adhesive film of intravenous cannulation to avoid patient's skin contact with the sensor patch. The advantages without skin contact of the sensor patch are less biocompatibility consideration of medical device and a faster regulatory approval period. The sensor patch may be portable, practical and cost-effective for routine intravenous (IV) cannulation usage. One or more radio frequency (RF) wireless modules may be integrated into the sensor patch for facilitating operator usage.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A sensor patch for detecting extravasation, the sensor patch comprising:
    an elastic film; and
    at least one sensing electrode disposed on the elastic film, wherein the at least one sensing electrode comprises a piezoresistive material,
    wherein the at least one sensing electrode is configured so that an electrical resistance of the at least one sensing electrode is changeable in response to a force acting on the at least one sensing electrode; and wherein the at least one sensing electrode is a single layer of metal printed on the elastic film, the layer of a thickness of less than 0.2 µm.

2. The sensor patch as claimed in claim 1, wherein the elastic film is adapted to conform to a contour of a surface on which the sensor patch is positioned.

3. The sensor patch as claimed in claim 1, wherein the sensor patch is stretchable.

4. The sensor patch as claimed in claim 1, wherein the at least one sensing electrode comprises a strain gauge.

5. The sensor patch as claimed in claim 1, further comprising an adhesive layer provided on one side of the elastic film.

6. The sensor patch as claimed in claim 5, wherein the at least one sensing electrode is disposed on another side of the elastic film opposite to the one side of the elastic film.

7. The sensor patch as claimed in claim 1, further comprising at least one pair of bonding pads electrically coupled to the at least one sensing electrode.

8. The sensor patch as claimed in claim 1, wherein the at least one sensing electrode is formed into an arrangement having at least one of a linear pattern, a curved pattern, a meander pattern, a zig zag pattern or a spiral pattern.

9. The sensor patch as claimed in claim 1, wherein a width of the at least one sensing electrode is between about 0.5 mm and about 10 mm.

10. The sensor patch as claimed in claim 1, wherein the electrical resistance of the at least one sensing electrode is changeable in response to at least one of a normal force or a shear force acting on the at least one sensing electrode.

11. The sensor patch as claimed in claim 1, wherein the electrical resistance of the at least one sensing electrode is changeable in response to one or more forces acting on the at least one sensing electrode in x-, y- and z-directions of a three-dimensional Cartesian coordinate system.

12. The sensor patch as claimed in claim 1, wherein the sensor patch comprises a plurality of sensing electrodes.

13. The sensor patch as claimed in claim 1, wherein the sensor patch is a planar sensor patch.

14. The sensor patch as claimed in claim 1, wherein the thickness of the metal layer is at least substantially uniform throughout the at least one sensing electrode.

15. A sensing device comprising:
a sensor patch for detecting extravasation, the sensor patch comprising:
an elastic film; and
at least one sensing electrode disposed on the elastic film, wherein the at least one sensing electrode comprises a piezoresistive material,
wherein the at least one sensing electrode is configured so that an electrical resistance of the at least one sensing electrode is changeable in response to a force acting on the at least one sensing electrode; and
wherein the at least one sensing electrode is a single layer of metal printed on the elastic film, the layer of a thickness of less than 0.2 µm; and
a readout circuit for determining the electrical resistance of the at least one sensing electrode of the sensor patch.

16. The sensing device as claimed in claim 15, further comprising at least one of a visual means or an audio output means.

17. The sensing device as claimed in claim 15, further comprising a radio frequency wireless module electrically coupled to the readout circuit.

* * * * *